United States Patent [19]

Harris

[11] Patent Number: 5,414,095

[45] Date of Patent: May 9, 1995

[54] ANHYDRIDE-FUNCTIONAL PRIMARY ALKYL HALIDES

[75] Inventor: Rodney M. Harris, Chicago, Ill.

[73] Assignee: The Sherwin-Williams Company, Cleveland, Ohio

[21] Appl. No.: 176,408

[22] Filed: Jan. 3, 1994

[51] Int. Cl.[6] ............................................ C07D 307/60
[52] U.S. Cl. ...................................... 549/254; 562/596
[58] Field of Search ......................... 549/254; 562/596

[56] References Cited

U.S. PATENT DOCUMENTS

| | | | |
|---|---|---|---|
| 3,243,480 | 3/1966 | Anderson et al. | 260/869 |
| 3,256,506 | 6/1966 | Anderson et al. | 260/77.5 |
| 3,317,568 | 5/1967 | Wygant et al. | 260/346.8 |
| 3,644,493 | 2/1972 | Wygant et al. | 260/485 |
| 3,655,726 | 4/1972 | Wygant et al. | 260/468 |
| 4,209,411 | 6/1980 | Winans et al. | 252/56 |
| 4,661,275 | 4/1987 | Forsberg et al. | 252/49.3 |
| 4,664,826 | 5/1987 | Gutierrez et al. | 252/482 |
| 4,770,799 | 9/1988 | Farng et al. | 252/35 |

*Primary Examiner*—Bernard Dentz
*Attorney, Agent, or Firm*—Robert E. McDonald; Steven W. Tan; Heidi A. Boehlefeld

[57] ABSTRACT

An anhydride-functional primary alkyl halide having the structure:

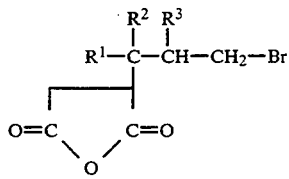

wherein $R^1$, $R^2$ and $R^2$ are each individually hydrogen or methyl, and the total number of carbon atoms in $R^1$ and $R^2$ and $R^3$ combined is two or less. The compounds are useful in the synthesis of polymers, etc.

4 Claims, No Drawings

ANHYDRIDE-FUNCTIONAL PRIMARY ALKYL HALIDES

BACKGROUND OF THE INVENTION

1. Field of the Invention

This invention involves novel anhydride-functional primary alkyl halides having the structure:

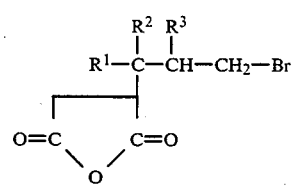

wherein $R^1$, $R^2$ and $R^3$ are each individually hydrogen, or methyl, and the total number of carbons in $R^1$ and $R^2$ and $R^3$ combined is two or less.

The anhydride-functional primary halides are useful as corrosion or scale inhibitors, thickeners, dispersants, neutralizing agents, and as crosslinking agents for compounds having functional groups, such as epoxide groups, which are reactive with anhydride groups. Additionally, due to the primary alkyl halide functionality, these compounds are especially useful as reactants in nucleophilic substitution reactions. In nucleophilic substitution reactions, these primary halides can be reacted with nucleophilic reagents, such as carboxylic acid salts, which are relatively unreactive with anhydride groups.

The anhydride-functional primary alkyl halides of this invention have a variety of potential applications due to their combination of reactive primary halide and reactive anhydride sites. Either the anhydride or the halide group could be reacted first, followed, if desired, by subsequent reaction of the other functionality. For example, the anhydride group could be reacted with hydroxyl groups on an alcohol or polyol to provide a product having a pendant primary alkyl halide group. Alternatively, the primary alkyl halide functionality could be reacted first, such as in an alkylation reaction with a carboxylic acid salt, to provide a product having pendant anhydride functionality. This anhydride-functional product could then be utilized as a crosslinker, for example, or the anhydride group could be hydrolyzed to produce a diacid-functional material. The relatively short alkyl chain length, the primary halide group, and the reactivity of the substituted succinic anhydride group combine to provide the unique properties of this material.

2. Description of the Prior Art

Alkyl substituted succinic anhydrides are known in the art. U.S. Pat. No. 4,209,411 teaches $C_{12}$ to $C_{22}$ 2-alkenyl-2,3-dialkyl or 2,3-cyclo-alkenyl substituted succinic acid anhydrides or corresponding acids and indicates that the olefin precursor could be halogenated prior to reaction with the maleic anhydride to produce the substituted succinic anhydride. U.S. Pat. No. 4,661,275 teaches $C_8$ to $C_{40}$ hydrocarbyl group substituted succinic anhydrides. The hydrocarbyl-based substituents could be derived from chlorinated olefins. U.S. Pat. No. 4,664,826 teaches hydrocarbon substituted succinic anhydride materials wherein the aliphatic group is typically a $C_2$ to about $C_{50}$ aliphatic hydrocarbon group which could contain a halogen. U.S. Pat. No. 4,770,799 teaches hydrocarbon substituted anhydride materials wherein the hydrocarbon groups contain from about 6 to about 42 carbon atoms and could include halogen substituents.

BRIEF SUMMARY OF THE INVENTION

This invention involves anhydride-functional primary halides. As a result of their primary halide nature, these materials are particularly useful as reactants in nucleophilic substitution reactions wherein a pendent anhydride group could be incorporated by the reaction. Due to the relatively short chain length of the alkyl substituent, the materials of this invention help to maximize the number of equivalents of anhydride which can be incorporated for a given weight of starting material.

It is therefore an object of this invention to provide a novel, primary halide. Another object is to provide a chemical product having both anhydride and primary alkyl halide substituents. These and other objects of the invention will become apparent from the following discussions.

DETAILED DESCRIPTION OF THE INVENTION

The anhydride-functional primary alkyl halides can be conveniently prepared by the Anti-Markovnikov addition of hydrogen bromide to an alkenyl succinic anhydride having the structure:

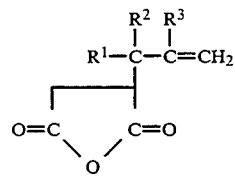

wherein $R^1$, $R^2$ and $R^3$ are each individually hydrogen, or methyl, and the total number of carbons in $R^1$ and $R^2$ and $R^3$ combined is two or less. The alkenyl succinic anhydride can be conveniently prepared by the ene reaction of succinic anhydride and an alkene. For example, the ene reaction of propylene and succinic anhydride will yield the desired allyl succinic anhydride product wherein $R^1$, $R^2$ and $R^3$ are each H. The ene reaction product when isobutene is the starting alkene yields the alkenyl succinic anhydride wherein $R^1$ and $R^2$ are each H and $R^3$ is methyl. The ene reaction product when 2-butene is the starting alkene yields the alkenyl succinic anhydride wherein $R^1$ is methyl and $R^2$ and $R^3$ are each H. Other useful ene reaction products can be produced using 2-methyl-2-butene as the starting olefin. Although it is preferred for many applications to minimize the molecular weight, and therefore, the equivalent weight, of the anhydride-functional primary bromide product, $R^1$, $R^2$ and $R^3$ groups longer than methyl could be utilized and such products can be conveniently prepared by selection of the appropriate olefin starting material.

Allyl succinic anhydride (sometimes called propenyl succinic anhydride) is especially preferred as the alkenyl succinic anhydride due to its reactivity and commercial availability. The synthesis of allyl succinic anhydride has been representatively taught by Alder, et al., Chem Ber. 1983, 76, 27; and Phillips, et al., J. Am. Chem. Soc. 1958, 80, 3663; and Anderson, et al., U.S. Pat. No. patent 3,243,480 issued March 29, 1966. The synthesis taught in these references involves the ene reaction, in a bomb at 200° C. for approximately 12 hours, of maleic anhydride and propylene in the presence of a diluent such as benzene and a polymerization inhibitor such as p-t-butylcatechol. Allyl succinic anhydride is commercially available from a variety of sources, including Polysciences, Inc. at 400 Valley Road, Warrington, Pa.; and from Wacher Chemicals (USA), Inc. at 50 Locust Avenue, New Haven, Conn.

The hydrogen bromide which is reacted with the alkenyl succinic anhydride to produce the halogenated alkyl succinic anhydride, is commercially available, or can be generated by contacting an aqueous hydrogen bromide solution with phosphorous pentoxide. The Anti-Markovnikov addition is typically accomplished by bubbling the hydrogen bromide gas into a cooled solvent solution of the alkenyl succinic anhydride in the presence of a peroxide catalyst, such as dibenzoyl peroxide, at temperatures typically ranging from about 10° C. to about 40° C.

The following examples have been selected to illustrate specific embodiments and practices of advantage to a more complete understanding of the invention. Unless otherwise stated, "parts" means parts-by-weight and "percent" is percent-by-weight.

EXAMPLE 1

2-(3-Bromopropyl)-Succinic Anhydride

A cooled (10° C.; ice/water) solution of 1200 g (8.56 mol) allyl succinic anhydride, 6500 ml of toluene (dried over MgSO$_4$), and 6.3 g of dibenzoyl peroxide in 100 ml of toluene was stirred under a nitrogen atmosphere. Next, hydrogen bromide gas was bubbled in (volatile contaminants and water condensed out of the gas by cooling a cold trap to −23° C. with CCl$_4$/dry ice bath) at a constant rate such that the reaction mixture absorbed all incoming hydrogen bromide (HBr) gas. After about two hours, an additional 2.0 grams, and again approximately two hours later 1.0 grams of dibenzoyl peroxide were added after the reaction temperature increased to about 15° C. A shiny beige solid formed as hydrogen bromide bubbling continued. The mixture was allowed to warm to room temperature. Shortly thereafter, FT-infrared analysis indicated essentially all of the vinyl groups were consumed, and the reaction was stopped.

Filtrating and drying the reaction mixture yielded 1533.5 g (81.0%) of beige solid bromopropyl succinic anhydride having a melting point of 91°–92.5° C. Crystallization of the solid from toluene (5 g solid/25 g toluene) gave 1275 g (67.3 % yield) of beige needles having a melting point of 92°–94° C. The material was characterized by FT-infrared and 1H NMR to be the desired 2-(3-bromopropyl)-succinic anhydride. The filtrate from the crystals was concentrated to give an additional 119.2 g (6.3 %) of dried bromopropyl anhydride beige crystals having a melting point of 89.5°–92.5° C.

As an example of the use of the primary alkyl halide in a nucleophilic substitution reaction, the product of Example 1, was converted to a polymerizable unsaturated anhydride-functional monomer as shown below.

EXAMPLE 2

2-(3-Methacryloxypropyl)-Succinic Anhydride

To a room temperature solution of 0.12 g of butylated hydroxy toluene, 55.0 g (0.638 moles) of methacrylic acid in 440 ml of toluene, and 57.2 g (0.565 moles) of triethylamine in 440 ml of toluene prepared under nitrogen, was added 110 g of the 2-(3-bromopropyl)-succinic anhydride of Example 1. The reaction was then stirred and heated at 100° C. for 12.5 hours. The reaction was then cooled to 40° C. and 11.00 g (0.127 moles) of methacrylic acid and 11.44 g (0.113 moles) of triethylamine were added to the flask and heated to 100° C. Heating at 100° C. was continued for an additional 6.5 hours. Progress of the reaction was followed by monitoring the intensity of the infrared C-0 band for the methacrylate ester at ∼1168 cm$^{-1}$.

The reaction mixture was then filtered and the collected salt was washed with toluene. The combined toluene filtrates were then washed with 500 ml of aq. NaCl solution, 3 × 1000 ml of an 4:1.5 (volume ratio) sat. NaCl/sat. NaHCO$_3$ solution, and a final washing with sat. NaCl solution, and then dried over MgSO$_4$. The volatiles were removed to give 76.49 g (68%) of a light brown liquid which was characterized by FT-infrared and NMR as the desired 2-(3-methacryloxypropyl)-succinic anhydride. The monomer prepared in this example could be subsequently polymerized with other unsaturated monomers to provide an anhydride-functional polymer.

While this invention has been described by a specific number of embodiments, it is obvious that other variations and modifications may be made without departing from the spirit and scope of the invention as set forth in the appended claims.

The invention claimed is:

1. An anhydride-functional primary alkyl halide having the structure:

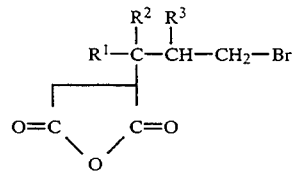

wherein $R^1$, $R^2$ and $R^3$ are each individually hydrogen or methyl and the total number of carbon atoms in $R^1$ and $R^2$ and $R^3$ combined is two or less.

2. The alkyl halide of claim 1 wherein $R^1$, $R^2$ and $R^3$ are each hydrogen.

3. The alkyl halide of claim 1 wherein $R^1$ and $R^2$ are hydrogen and $R^3$ is methyl.

4. The alkyl halide of claim 1 wherein $R^1$ is methyl and $R^2$ and $R^3$ are each hydrogen.

* * * * *